United States Patent [19]

Hurni et al.

[11] Patent Number: 4,861,706

[45] Date of Patent: Aug. 29, 1989

[54] ASSAY FOR HEPATITIS A VIRUS

[75] Inventors: William M. Hurni; William J. Miller, both of North Wales; William J. McAleer, Ambler, all of Pa.

[73] Assignee: Merck & Co., Inc., Rahway, N.J.

[21] Appl. No.: 857,695

[22] Filed: Apr. 29, 1986

Related U.S. Application Data

[63] Continuation-in-part of Ser. No. 296,602, Aug. 26, 1981, abandoned, and a continuation-in-part of Ser. No. 296,603, Aug. 26, 1981, abandoned.

[51] Int. Cl.[4] .......................... C12Q 1/70; C12N 7/00; C12R 1/91

[52] U.S. Cl. .......................................... 435/5; 435/235; 435/948

[58] Field of Search .................... 435/5, 29, 34, 39, 40, 435/235, 236, 238, 948; 424/2

[56] References Cited

U.S. PATENT DOCUMENTS 3,651,212 3/1972 Meyer et al. ............................ 435/5

OTHER PUBLICATIONS

Fenner et al., Medical Virology, pp. 70 and 33 and 67–68 (1970) Academic Press, NY.

Marcus et al., Journal of Virology (4–1967), pp. 334–343.

Berthold et al., Proc. Soc. Exp. Biol. Med. 143, pp. 698–700 (1973).

Fuerst, Microbiology in Health and Disease, pp. 389–392 (1978), W. B. Saunders Co., Philadelphia.

Kumagai et al., Journal of Immunology 87, pp. 245–256 (1961).

Hermodsson, Virology 20, pp. 333–343 (1963).

Maeno et al., Virology 29, pp. 255–263 (1966).

Locarnini et al., Journal of Virology 37(1) pp. 216–225 (1981).

*Primary Examiner*—John Edward Tarcza

*Attorney, Agent, or Firm*—Frank S. Chow; Hesna J. Pfeiffer

[57] ABSTRACT

A quantitative assay for HAV comprises infecting at a temperature of from about 30° to about 37° C. a cell sheet with a dilution series of hepatitis A virus and then adding Newcastle disease virus (NDV) to the infected cell sheet and incubating the infected cell sheet in the presence of NDV at an elevated temperature for a time sufficient to permit a cytopathic effect (CPE) to become manifest, this time typically being at least about 4 days and preferably about 5 days. At an incubation temperature of from about 31° to about 33° C. the absence of CPE indicates the presence of HAV and the presence of CPE indicates the absence of HAV. At an incubation temperature of from about 34° to about 36° C. the absence of CPE indicates the absence of HAV and the presence of CPE indicates the presence of HAV.

5 Claims, No Drawings

ASSAY FOR HEPATITIS A VIRUS

RELATED APPLICATIONS

The present patent application is a continuation-in-part of copending U.S. patent applications 296,602 and 296,603 filed 26 August 1981 now abandoned.

BACKGROUND OF THE INVENTION

It is known that one can determine the titer of a virus by determining the extent of cytopathic effect (CPE) using serial dilutions of the virus to infect a susceptible tissue culture. This technique cannot be used, however, for hepatitis A virus (HAV) which infects cells without producing a visible CPE. Marcus and Carver have described this interference phenomenon for rubella virus, J. Virol., April 1967, pp. 334–343. When cells were infected with rubella virus, the rubella infection rendered the cells refractory to subsequent Bunyamwera virus infection. A difficulty with an interference assay, however, is that not all cell sheets infected with a first virus prevent growth of the second virus with the result that there is no difference in CPE between cells infected with the first virus and uninfected cells. Moreover, an interference assay is not absolutely specific for the virus in question and it is a difficult assay to develop and Perform. Enhancement assays for hog cholera virus have been described by Kumagai et al., J. Immunol. 87:245 (1961) and Matumoto et al.. J. Immunol 87:257 (1961).

OBJECTS OF THE INVENTION

It is, accordingly, an object of the present invention to provide an improved assay for hepatitis A virus which does not produce visible CPE. A further object is to provide an assay for hepatitis A virus which produces an interference effect at one temperature range and an enhancement effect at a different temperature range. These and other objects of the present invention will be apparent from the following description.

SUMMARY OF THE INVENTION

A quantitative assay for HAV comprises infecting at a temperature of from about 30° to about 37° C. a cell sheet with a dilution series of hepatitis A virus and then adding Newcastle disease virus (NDV) to the infected cell sheet and incubating the infected cell sheet in the presence of NDV at an elevated temperature for a time sufficient to permit a cytopathic effect (CPE) to become manifest, this time typically being at least about 4 days and Preferably about 5 days. At an incubation temperature of from about 31° to about 33° C. the absence of CPE indicates the presence of HAV and the gPresence of CPE indicates the absence of HAV. At an incubation temperature of from about 34° to about 36° C. the absence of CPE indicates the absence of HAV and the presence of CPE indicates the Presence of HAV.

DETAILED DESCRIPTION

The assay of the present invention is suitably carried out in a multi-well assay plate containing a cell sheet formed of MRC-5 or WI-38 cells. A dilution series of HAV is added to the wells of the assay plate along with MRC-5 cells. The cells and HAV are incubated either at from about 31° to about 33° C. or from about 34° to about 36° C. Approximately 2 days after planting, the medium is replaced. The plate is incubated at whichever of the foregoing temperatures was selected for a period of time sufficient to permit the virus to infect the cells. Generally, this requires up to about four weeks. It is generally preferable to replenish the medium at least once during the incubation period required to infect the cell sheet. When the incubation period is complete, the incubation medium is aspirated off and fresh medium containing NDV is added to each well. The assay late is then incubated at the previously selected temperature for a period of time sufficient to permit CPE to develop. Usually this takes several days, generally at least about four days. The assay plate is then read for CPE. When the selected temperature is from about 31° to about 33° C. the absence of CPE indicates the Presence of HAV and the presence of CPE indicates the absence of HAV. When the selected temperature is from about 34° to about 36° C. the absence of CPE indicates the absence of HAV and the presence of CPE indicates the Presence of HAV.

It has been found that some common interference viruses such as Vesicular Stomatitis and Bunyamwera viruses cannot be used. The interference assay of the present invention which is selected when the temperature is from about 31° to about 33° C. requires the use of NDV.

The following example illustrates the present invention without, however, limiting the same thereto.

EXAMPLE

An initial 1:100 dilution of the virus is made by adding 100 μl of virus suspension to 9.9 ml of Williams Medium E (WME) plus 1% L-glutamine (2.92 mg/ml), 1/2 % fetal calf serum (FCS) and 50 μg/ml neomycin. From this initial $10^{-2}$ dilution, serial 10-fold dilutions are made by transferring 1 ml of virus suspension to 9 ml of WME. Seven 10-fold dilutions are made covering the range of $10^{-2}$–$10^{-8}$. 75μl of a $10^{-2}$ suspension of virus is added to each of 12 wells in row A of a multi-well assa Y Plate. 75μl of a $10^{-3}$ dilution of virus suspension is added to each of 12 wells in row B and so on until rows A through G have been filled with dilutions of virus from $10^{-2}$-$10^{-8}$. All wells in row H, which is the control row, are filled with 75μl of WME. 75 μl/well of 200,000 MRC-5 cells/ml in Basal Medium Eagle with Earle's Balanced Salt Solution +10% FCS +1% L-glutamine (29.2 mg/ml) +50 μg/ml neomycin are added to all wells. The plates are then placed in a humidified 5% $Co_2$ incubator for a two day incubation period at either 32° C. or 35° C. The plates are then removed from the incubator, the media aspirated from the wells and plates are refed with WME and returned to the incubator for a two week incubation at the previously selected temperature. At the end of the 2 week incubation period, the plates are refed as above and returned to the incubator for a second 2 week incubation period. After the second 2 week incubation period, the plates are ready for the addition of NDV to reveal the presence of HAV. In the interference method (the selected temperature is 32° C.), the NDV, California strain, stock irus suspension is thawed and diluted in WME to a concentration of 106 TCID In the enhancement assay (the selected temperature is 35° C.), the NDV, California strain, stock virus suspension is thawed and diluted in WME to a concentration of 104 TCID50/ml WME is aspirated from the wells of the plates and 150 μl of the above virus suspension is Placed in all wells of all plates. The plates are then incubated at the previously selected temperature for 5 days. After this incubation period, the plate is read microscopically. At a temperature of 32° C. where NDV CPE is absent, HAV is present and, conversely, hwere NDV CPE is present, HAV is absent. At a temperature of 35° C. where NDV CPE is absent, HAV is absent and, conversely, where NDV CPE is present, HAV is present.

The following readings are obtained at 32° C. wherein a - sign indicates the presence of HAV (determined by the absence of CPE) and a +sign indicates the absence of HAV (determined by the presence of CPE):

| Row | HAV Conc. | Column 1 | 2 | 3 | 4 | 5 | 6 | 7 | 8 | 9 | 10 | 11 | 12 |
|---|---|---|---|---|---|---|---|---|---|---|---|---|---|
| 1 | $10^{-2}$ | − | − | − | − | − | − | − | − | − | − | − | − |
| 2 | $10^{-3}$ | − | − | − | − | − | − | − | − | − | − | − | − |
| 3 | $10^{-4}$ | − | − | − | − | − | − | − | − | − | − | − | − |
| 4 | $10^{-5}$ | − | − | + | − | + | + | − | + | − | + | − | + |
| 5 | $10^{-6}$ | + | + | + | + | + | + | + | + | + | + | + | + |
| 6 | $10^{-7}$ | + | + | + | + | + | + | + | + | + | + | + | + |
| 7 | $10^{-8}$ | + | + | + | + | + | + | + | + | + | + | + | + |
| 8* | 0 | + | + | + | + | + | + | + | + | + | + | + | + |

*Control Row containing cells and NDV but no HAV.

The titer of the HAV virus is then calculated using methods known to those skilled in the art such as the Reid and Meunch method.

The following readings are obtained at 35° C. wherein a - sign indicates the absence of HAV (determined by the absence of CPE) and a +sign indicates the presence of HAV (determined by the presence of CPE):

| Row | HAV Conc. | Column 1 | 2 | 3 | 4 | 5 | 6 | 7 | 8 | 9 | 10 | 11 | 12 |
|---|---|---|---|---|---|---|---|---|---|---|---|---|---|
| 1 | $10^{-2}$ | + | + | + | + | + | + | + | + | + | + | + | + |
| 2 | $10^{-3}$ | + | + | + | + | + | + | + | + | + | + | + | + |
| 3 | $10^{-4}$ | + | + | + | + | + | + | + | + | + | + | + | + |
| 4 | $10^{-5}$ | + | + | − | + | − | − | + | − | + | − | + | − |
| 5 | $10^{-6}$ | − | − | − | − | − | − | − | − | − | − | − | − |
| 6 | $10^{-7}$ | − | − | − | − | − | − | − | − | − | − | − | − |
| 7 | $10^{-8}$ | − | − | − | − | − | − | − | − | − | − | − | − |
| 8* | 0 | − | − | − | − | − | − | − | − | − | − | − | − |

-continued

*Control Row containing cells and NDV but no HAV.

The titer of the HAV virus is then calculated using methods known the those skilled in the art such as the Reid and Meunch method.

What is claimed is:

1. A method for carrying out an assay for HAV comprising (A) adding to cell sheets in a multi-well assay plate a dilution series of a sample to be tested for the presence of hepatitis A virus, allowing hepatitis A virus if present in the sample to infect the cell sheets, adding NDV to the cell sheets and incubating the cell sheets in the presence of NDV at a temperature of from about 31 to 33° C. for a time sufficient to permit CPE to become manifest; and (b) repeating (a) repeating (a) at from 34° to about 36° C. for a time sufficient to permit CPE to become manifest wherein the absence of CPE indicating the presence of HAV, and the presence of CPE indicating the absence of HAV at a selected temperature of from about 31° to 33° C., and the absence of CPE indicating the absence of HAV and the presence of CPE indicating the presence of HAV at a selected temperature of from about 34° to about 36° C.

2. A method according to claim 1 wherein the time for infection of the cell sheets with HAV to become manifest is up to about 4 weeks.

3. A method according to claim 1 wherein the time sufficient to permit CPE to become manifest is at least about 4 days.

4. A method according to claim 1 wherein the quantity of NDV is about 106 TCID50/ml for the arsey to be run in the temperature from about 31° to 33° C. and wherein the quantity of NDV is about 104 TCID50/ml for the assay to be run at the temperature range of 34° to about 36° C.

5. A method according to claim 1 wherein the titer of hepatitis A virus is measured by deermining the lowest dilution of NDV which fails to produce CPE when the temperature range is from about 31° to 33° and is measured by determining the lowest dilution of NDV which produces CPE when the temperature range is from 34° to about 36° C.

* * * * *